(12) United States Patent
Murray et al.

(10) Patent No.: US 6,709,669 B1
(45) Date of Patent: Mar. 23, 2004

(54) FAST-DISPERSING DOSAGE FORMS CONTAINING FISH GELATIN

(75) Inventors: Owen Murray, Swindon (GB); Michael Hall, Swindon (GB); Patrick Kearney, Swindon (GB); Richard Green, Fordwich (GB)

(73) Assignee: R. P. Scherer Technologies, Inc., Las Vegas, NV (US)

( * ) Notice: Subject to any disclaimer, the term of this patent is extended or adjusted under 35 U.S.C. 154(b) by 0 days.

(21) Appl. No.: 09/959,018

(22) PCT Filed: Apr. 7, 2000

(86) PCT No.: PCT/US00/09278
§ 371 (c)(1),
(2), (4) Date: Oct. 16, 2001

(87) PCT Pub. No.: WO00/61117
PCT Pub. Date: Oct. 19, 2000

(51) Int. Cl.[7] .................. A61K 9/64; A61K 9/22; A61K 9/14; A61K 9/20

(52) U.S. Cl. ............ 424/434; 424/464; 424/456; 424/465; 424/484; 424/489; 424/468

(58) Field of Search ............... 424/434, 464, 424/456, 465, 484, 489, 468

(56) References Cited

U.S. PATENT DOCUMENTS

| | | | |
|---|---|---|---|
| 3,885,026 A | 5/1975 | Heinemann et al. | 424/14 |
| 4,134,943 A | 1/1979 | Knitsch et al. | 264/28 |
| 4,935,243 A | 6/1990 | Borkan et al. | 424/441 |
| 5,079,018 A | 1/1992 | Ecanow | 426/385 |
| 5,093,474 A | 3/1992 | Grossman et al. | 530/355 |
| 5,298,261 A | 3/1994 | Pebley et al. | 424/488 |
| 5,348,852 A | 9/1994 | Bonderman | 435/4 |
| 5,382,437 A | 1/1995 | Ecanow | 424/499 |
| 5,478,569 A * | 12/1995 | Berneis et al. | 424/456 |
| 5,484,888 A | 1/1996 | Holzer | 530/355 |
| 5,587,180 A * | 12/1996 | Allen, Jr. et al. | 424/499 |
| 5,595,761 A | 1/1997 | Allen, Jr. et al. | 424/484 |
| 6,020,003 A * | 2/2000 | Stroh et al. | 424/489 |
| 6,284,270 B1 * | 9/2001 | Lagoviyer et al. | 424/464 |

FOREIGN PATENT DOCUMENTS

| | | |
|---|---|---|
| EP | 0 346 879 A1 | 12/1989 |
| EP | 0 347 751 A1 | 12/1989 |
| EP | 0 548 356 B1 | 6/1991 |
| EP | 0 690 747 B1 | 1/1996 |
| EP | 0 841 010 A1 | 11/1996 |
| GB | 1 548 022 | 7/1979 |
| WO | WO 93/12769 | 7/1993 |
| WO | WO 93/13758 | 7/1993 |
| WO | WO 94/14422 | 7/1994 |
| WO | WO 96/20612 | 7/1996 |
| WO | WO 99/07348 | 2/1999 |

OTHER PUBLICATIONS

US 5,120,549, 6/1992, Gole et al. (withdrawn)

* cited by examiner

Primary Examiner—Thurman K. Page
Assistant Examiner—Blessing Fubara
(74) Attorney, Agent, or Firm—Donald O. Nickey; Andrew G. Rozycki

(57) ABSTRACT

The invention disclosed herein relates to a pharmaceutical composition comprising a carrier and an active ingredient, wherein the carrier is fish gelatin and the composition is a fast-dispersing dosage form designed to release the active ingredient rapidly on contact with a fluid. In one embodiment, the composition is designed for oral administration and releases the active ingredient rapidly in the oral cavity on contact with saliva. The fish gelatin can be obtained from cold water fish sources and is preferably the non-gelling, non-hydrolyzed form. A process for preparing such a composition and a method of using fish gelatin in a fast dispersing dosage form are also provided.

7 Claims, No Drawings

FAST-DISPERSING DOSAGE FORMS CONTAINING FISH GELATIN

TECHNICAL FIELD

This invention relates to fast dispersing pharmaceutical compositions. In particular, the invention relates to freeze-dried fast-dispersing dosage forms containing fish gelatin.

BACKGROUND OF THE INVENTION

Fast-dispersing dosage forms which are designed to release the active ingredient in the oral cavity are well known and can be used to deliver a wide range of drugs. Many such fast-dispersing dosage forms utilize gelatin as a carrier. Gelatin B. P., which is normally utilized in such formulations, is defined as a protein obtained by partial hydrolysis of animal collagenous tissues such as skin, tendons, ligaments and bones, with boiling water. However, such mammalian derived gelatin has an unpleasant taste and thus necessitates the use of sweeteners and flavors in such fast-dispersing dosage forms to mask the taste of the gelatin in addition to any sweeteners and flavors which may be required to mask the taste of the active ingredient. Moreover, when conventional mammalian derived gelatin is used in the production of such fast-dispersing dosage forms, it is necessary to heat the gelatin solution to 60° C. in order to effect solution This heating step increases processing times and incurs heating costs thereby increasing the overall costs of the process.

U.S. Pat. No. 5,120,549 to Gole et al. discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix forming elements and active ingredient being substantially insoluble in the second solvent, whereby the first solvent is substantially removed resulting in a fast-dispersing matrix.

U.S. Pat. No. 5,079,018 to Ecanow discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in the place of the hydration liquid.

Published International Application No. WO 93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 to Pebley et al. discloses fast-dispersing dosage forms which comprise a partially collapsed matrix network that has been vacuum dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

U.S. Pat. No. 5,595,761 to Allen Jr. et al. discloses a particulate support matrix for use in making a rapidly dissolving tablet, comprising a first polypeptide component having a net charge when in solution, e.g. non-hydrolyzed gelatin; a second polypeptide component having a net charge of the same sign as the net charge of the first polypeptide component when in solution e.g. hydrolyzed gelatin; and a bulking agent, and wherein the first polypeptide component and the second polypeptide component together comprise about 2% to 20% by weight of the particulate support matrix and wherein the bulking agent comprises about 60% to 96% by weight of the particulate support matrix; and wherein the second polypeptide component has a solubility in aqueous solution greater than that of the first polypeptide component and wherein the mass to mass ratio of the first polypeptide component to the second polypeptide component is from about 2:1 to about 1:14; and wherein when the support matrix is introduced into an aqueous environment the support matrix disintegrates within less than about 20 seconds.

EP 0 690 747 B1 to Nguyen et al. describes particles comprising an excipient forming a matrix and at least one active ingredient uniformly distributed in the mass of the matrix which are prepared by a process comprising the steps of preparing a homogenous pasty mixture with a viscosity below 1 Pa.s measured at room temperature (15–20° C.), at least one active ingredient, a physiologically acceptable hydrophilic excipient and water; extruding the resulting homogenous mixture and cutting the extrudate to give moist particles; freezing the resulting particles as they fall under gravity through a stream of inert gas at a temperature below 0° C.; and drying the particles by freeze drying.

Australian Patent No. 666,666 discloses a rapidly disintegratable multiparticulate tablet having a mixture of excipients in which the active substance is present in the form of coated microcrystals or optionally coated microgranules. Such tablets are thought to disintegrate in the mouth in typically less than 60 seconds.

U.S. Pat. No. 5,382,437 to Ecanow discloses a porous carrier material having sufficient rigidity for carrying and administering an active agent which is capable of rapid dissolution by saliva. The porous carrier material of Ecanow is formed by freezing a liquified ammonia solution comprising liquid ammonia, liquid ammonia soluble gel or foam material, and a rigidifying agent for the gel or foam material selected from the group consisting of a monosaccharide, a polysaccharide and combinations thereof, and deammoniating the frozen material thus formed, by causing material transfer of ammonia from the frozen state to the gas state thereby leaving spaces in the carrier material in place of the frozen ammonia.

Published International Application No. WO 93/13758 (PCT/US92/07497) describes tablets of increased physical strength which are prepared by combining and compressing a meltable binder, excipients and a pharmaceutically active agent into a tablet, melting the binder into the tablet and then solidifying the binder. In one embodiment, a disintegrating agent is utilized to increase the disintegration rate of the tablet after oral intake. In another embodiment, a volatizable component is used to form porous tablets. Some embodiments disintegrate in the mouth in less than 10 seconds.

U.S. Pat. No. 3,885,026 to Heinemann et al. and U.S. Pat. No. 4,134,943 to Knitsch et al. also disclose fast-dispersing porous tablets and a method for increasing their physical strength by first compressing the tablet and then volatilizing a readily volatilizable solid adjuvant incorporated in the tablet to attain the desired porosity.

Published International Application No. WO 94/14422 describes a process for drying frozen discrete units in which the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

While the prior art is replete with methods and techniques for the preparation of rapidly dispersing dosage forms, it has failed to consider the benefits associated with the use of fish gelatin, especially non-gelling, non-hydrolyzed fish gelatin, in such dosage forms. The pharmaceutical industry would be able to avoid the use of mammalian derived gelatin due to taste considerations. Thus, there exists the need for improved fast-dispersing dosage forms which are designed to quickly release the active ingredient in the oral cavity that avoid the use of mammalian derived gelatin.

SUMMARY OF THE INVENTION

It has now been found that many of the problems associated with the use of mammalian-derived gelatin can be overcome if fish gelatin, especially non-gelling fish gelatin, is utilized for preparing fast-dispersing dosage forms. Surprisingly, the non-gelling form of fish gelatin from sources such as cold water fish, can be advantageously used in rapidly disintegrating dosage forms. Moreover, a number of further advantages have been identified in terms of processing parameters and the qualities of the resultant product.

The present invention discloses a pharmaceutical composition comprising a carrier and an active ingredient (e.g., drug, compound, and the like) wherein the carrier is fish gelatin and the composition is in the form of a fast-dispersing dosage form which releases the active ingredient rapidly on contact with a fluid (e.g., saliva, bodily fluids, water, and the like). Preferably, the composition is designed for oral administration and releases the active ingredient rapidly in the oral cavity. In another embodiment, the composition can be applied topically, for instance, to wet skin, or dispersed or dissolved in a liquid prior to topical or oral administration.

The invention also discloses a process for preparing fast-dispersing dosage forms by freeze-drying or lyophilizing a combination of the active ingredient and fish gelatin (e.g., non-gelling fish gelatin).

The invention further includes a method of using fish gelatin (e.g., non-gelling fish gelatin) in pharmaceutical compositions in fast dispersing dosage form, and in particular, freeze dried fast-dispersing dosage forms.

In a preferred embodiment, the composition of the invention is a solid fast-dispersing dosage form containing a network of the active ingredient and a water-soluble or water-dispersible carrier comprising fish gelatin (e.g., non-gelling fish gelatin), the network having been obtained by subliming solvent from a composition in the solid state containing the active ingredient and a solution or dispersion of the carrier in a solvent.

The fish gelatin used in accordance with the invention is preferably obtained from cold water fish sources and is the non-gelling type of fish gelatin. More preferably, the non-hydrolyzed form of non-gelling fish gelatin is used. In an alternative embodiment, spray-dried non-hydrolyzed non-gelling fish gelatin can be used.

DETAILED DESCRIPTION OF THE INVENTION

The phrase "fast-dispersing dosage form" refers to compositions which disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration. In a general context, the phrase encompasses all the previously mentioned dosage forms described herein as well as any other equivalent dosage form.

In a preferred embodiment, the compositions of the invention are solid fast-dispersing dosage forms comprising a solid network of the active ingredient and a water-soluble or water-dispersible carrier containing fish gelatin. Accordingly, the carrier is inert towards the active ingredient. The network is obtained by subliming solvent from a composition in the solid state, the composition comprising the active ingredient and a solution of the carrier in the solvent. The dosage forms according to the invention can be prepared according to the process disclosed in Gregory et al., U.K. Patent No. 1,548,022 using fish gelatin as the carrier.

Accordingly, an initial composition (or admixture) comprising the active ingredient and a solution of the fish gelatin carrier in a solvent is prepared followed by sublimation. The sublimation is preferably carried out by freeze drying the composition. The composition can be contained in a mold during the freeze-drying process to produce a solid form in any desired shape. The mold can be cooled using liquid nitrogen or solid carbon dioxide in a preliminary step prior to the deposition of the composition therein. After freezing the mold and composition, they are next subjected to reduced pressure and, if desired, controlled application of heat to aid in sublimation of solvent. The reduced pressure applied in the process can be below about 4 mm Hg, preferably below about 0.3 mm Hg. The freeze dried compositions can then be removed from the mold if desired or stored therein until later use.

When the process is used with active ingredients and fish gelatin as the carrier, a solid fast-dispersing dosage form is produced having the advantages associated with the use of fish gelatin described herein. Generally, fish gelatin is categorized as being from cold water and warm water fish sources and as being of the gelling or non-gelling variety. The non-gelling variety of fish gelatin, in comparison to gelling fish gelatin and bovine gelatin, contains lower proline and hydroxyproline amino acid content, which are known to be associated with cross-linking properties and gelling ability. Non-gelling fish gelatin can remain at solution concentrations of up to about 40% as well as in temperatures as low as 20° C. The fish gelatin used in accordance with the invention is preferably obtained from cold water fish sources and is the non-gelling type of fish gelatin. More preferably, the non-hydrolyzed form of non-gelling fish gelatin is used. In an alternative embodiment, spray-dried non-hydrolyzed non-gelling fish gelatin can be used. Fish gelatins suitable for use in the invention can be obtained from Croda Colloids Ltd. (Chesire, England), for example.

TABLE 1

| Amino Acid | Gelling Fish Gelatin | Bovine Gelatin | Non-Gelling Fish Gelatin |
|---|---|---|---|
| Aspartic Acid | 46.0 | 46.0 | 52.0 |
| Threonine | 26.0 | 16.9 | 25.0 |
| Serine | 37.0 | 36.5 | 69.0 |
| Glutamic Acid | 66.0 | 70.7 | 75.0 |
| Proline | 119.0 | 129.0 | 102.0 |

TABLE 1-continued

| Amino Acid | Gelling Fish Gelatin | Bovine Gelatin | Non-Gelling Fish Gelatin |
|---|---|---|---|
| Glycine | 343.0 | 333.0 | 345.0 |
| Alanine | 121.0 | 112.0 | 107.0 |
| Valine | 17.0 | 20.1 | 19.0 |
| Methionine | 9.5 | 5.5 | 13.0 |
| Isoleucine | 8.0 | 12.0 | 11.0 |
| Leucine | 23.0 | 23.1 | 23.0 |
| Tyrosine | 3.0 | 1.5 | 3.5 |
| Phenylalanine | 12.0 | 12.3 | 13.0 |
| Histidine | 9.5 | 4.5 | 7.5 |
| Lysine | 25.0 | 27.8 | 25.0 |
| Arginine | 54.0 | 46.2 | 51.0 |
| Hydroxyproline | 76.0 | 97.6 | 53.0 |
| Hydroxylysine | 7.5 | 5.5 | 6.0 |

Despite the comparatively lower proline and hydroxyproline content and other differences in non-gelling fish gelatin as compared to gelling fish gelatin and bovine gelatin, non-gelling fish gelatin can be successfully used in a matrix for preparing fast-dispersing dosage forms in accordance with the invention.

The composition according to the invention can also contain, in addition to the active ingredient and fish gelatin carrier, other matrix forming agents and secondary components. Matrix forming agents suitable for use in the present invention include materials derived from animal or vegetable proteins, such as other gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other materials which may also be incorporated into the composition of the present invention include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification (freezing). The matrix forming agent may be present in addition to a surfactant or to the exclusion of a surfactant. In addition to forming the matrix, the matrix forming agent may aid in maintaining the dispersion of any active ingredient within the solution of suspension. This is especially helpful in the case of active agents that are not sufficiently soluble in water and must, therefore, be suspended rather than dissolved.

Secondary components such as preservatives, antioxidants, surfactants, viscosity enhancers, coloring agents, flavoring agents, pH modifiers, sweeteners or taste-masking agents may also be incorporated into the composition. Suitable coloring agents include red, black and yellow iron oxides and FD & C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include the edible acids and bases, such as citric acid, tartaric acid, phosphoric acid, hydrochloric acid, maleic acid and sodium hydroxide. Suitable sweeteners include aspartame, acesulfame K and thaumatin. Suitable taste-masking agents in include sodium bicarbonate, ion exchange resins, cyclodextrin inclusion compounds, adsorbates or microencapsulated actives.

A variety of drugs can be can be used as the active ingredient in the composition of the present invention, including but not limited to analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, anti-hypertensive agents, anti-malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants. Specific examples of these drugs are found below:

Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac.

Antacids: aluminum hydroxide, magnesium carbonate, magnesium trisilicate, hydrotalcite, dimethicone.

Anthelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, notriptyline HCl, trazodone HCl, trimipramine maleate.

Anti-diabetics: acetohexamide, chlorpropamide, glibenclamide, gliclazide, glipizide, tolazamide, tolbutamide.

Anti-diarrheals: codeine phosphate, co-phenotrope, loperamide hydrochloride, suphasolazine, mesalazine, olsalazine, corticosteroids, prednisolone.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-malarials: amodiaquine, chloroquine, chloroproguanil HCl, halofantrine HCl, mefloquine HCl, proguanil HCl, pyrimetharmine, quinine sulphate.

Anti-migrane agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscine butyl bromide, hyoscyamine, mepenzolate bromide, orphenadrine, oxyphencylcimine HCl, tropicamide.

Anti-neoplastic agents and Immunosuppressants: aminoglutethimide, amsacrine, azathioprene, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, ornidazole, tinidazole.

Anti-rheumatics: ibuprofen, aceclofenac, acemetacin, azapropazone, diclofenac sodium, diflunisal, etodolac, ketoprofen, indomethacin, mefenamic acid, naproxen, piroxicam, aspirin, benorylate, auranofin, penicillamine.

Anti-thyroid agents: carbimazole, propylthiouracil.

Antivirals: acyclovir, amantadine hydrochloride, famciclovir, zidovadine, didanosine, zalcitabine, foscarnet sodium.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpride, temazepam, thioridazine, triazolam, zopiclone.

β-Blockers: acebutolol, alprenolol, atenolol, labetalol, metoprolol, nadolol, oxprenolol, pindolol, propanolol.

Cardiac inotropic agents: amrinone, digitoxin, digoxin, enoximone, lanatoside C, medigoxin.

Corticosteroids: beclomethasone, betanethasone, budesonide, cortisone acetate, desoxymethasone, dexarnethasone, fludrocortisone acetate, flunisolide, flucortolone, fluticasone propionate, hydrocortisone, methylprednisolone, prednisolone, prednisone, triamcinolone.

Cough suprressants: codeine phosphate, pholcodine, diamorphine, methadone.

Cytotoxics: ifosfamide, chlorambucil, melphalan, busulphan, cytotoxic antibodies, doxorubicin, epirubicin, plicamycin, bleomycin, methotrexate, cytarabine, fludarabine, gencitabine, fluorouracil, mercaptopurine, thioguanine, vincristine, vinblastine, vindesine, etoposide.

Decongestants: pseudoephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Anti-parkinsonian agents: brornocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [beta-(fluoromethylene)-3,4-dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine.

Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Lipid regulating agents: bezafibrate, clofibrate, fenofibrate, gemfibrozil, probucol.

Local anaesthetics: amethocaine, amylocaine, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocaine, ethyl chloride, ethyl p-piperidinoacetylaminobenzoate, etidocaine, hexylcaine, isobutamben, ketocaine, lignocaine, mepivacaine, meprylcaine, myrtecaine, octacaine, oxethazaine, oxybuprocaine, parethoxycaine, pramoxine, prilocaine, procaine, propranocaine, propoxycaine, proxymetacaine, ropivacaine, tolycaine, tricaine, trimecaine, vadocaine.

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamins, such as vitamin A, vitamin $B_2$, vitamin D, vitamin E, vitamin K, minerals.

Opioid analgesics: codeine, dextropropyoxyphene, diamorphine, dihydrocodeinc, meptazinol, methadone, morphine, nalbuphine, pentazocine.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli*, Pneumnococcal Disease, Mumps, Chikungunya, Hayfever, Asthma, Rheumatoid Arthritis, Carcinomas, Coccidiosis, Newcastle Disease, Enzotic pneumonia, Feline leukemia, Atrophic rhinitis, Erysipelas, Foot and Mouth disease and Swine pneumonia, or to prevent or reduce the symptoms of diseases caused by Vibrio species, Salmonella species, Bordetella species, Haemophilus species, *Toxoplasmosis gondii*, Cytomegalovirus, Chlamydia species, Streptococcal species, Norwalk Virus, *Escherichia coli, Helicobacter pylori*, Rotavirus, *Neisseria gonorrhae, Neisseria meningiditis*, Adenovirus, Epstein Barr Virus, Japanese Encephalitis Virus, *Pneumocystis carini*, Herpes simplex, Clostridia species, Respiratory Syncytial Virus, Klebsiella species, Shigella species, *Pseudomonas aeruginosa*, Parvovirus, Campylobacter species, Rickettsia species, Varicella zoster, Yersinia species, Ross River Virus, J.C. Virus, Rhodococcus equi, *Moraxella catarrhalis*, *Borrelia burgdorferi* and *Pasteurella haemolytica*.

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules.

Sex hormones and Contraceptives: clomiphene citrate, danazol, desogestrel, ethinyloestradiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, progesterone, stanozolol, stilboestrol, testosterone, tibolone.

Spermicides: nonoxynol 9.

Stimulants: amphetamine, dexamphetamine, dexfenfluramine, fenfluramine, mazindol, pemoline.

The precise quantity of active ingredient will vary according to the particular drug selected and the patient's needs. However, the active ingredient can be generally present in an amount from about 0.2% to about 95%, typically from about 1% to about 20%, by weight of the composition of the dried dosage form. The invention is further illustrated by the following Examples.

EXAMPLE 1

Preparation of a Placebo Fast-Disnersing Dosage Form using Fish Gelatin

Spray-dried fish gelatin (4 g) and mannitol (3 g) were added to a glass beaker. Purified water (93 g) was then added and solution effected by stirring using a magnetic follower. No heating was required. A Gilson pipette was then used to deliver 500 mg of this solution into each one of a series of preformed blister pockets having a pocket diameter of about 16 mm. The blister laminate comprised PVC coated with PVdC. The dosed units were then frozen at a temperature of −110° C. in a freeze tunnel with a residence time of 3.2 minutes and the frozen units were then held in an upright freezer for a time greater than 1.5 hours at a temperature of −25° C. (±5° C.). The units were then freeze-dried overnight with an initial shelf temperature of −10° C. rising to +20° C. at a pressure of 0.5 mbar. The units were checked for moisture prior to unloading by the drying trace and by the pressurized moisture check. The resultant units had the following composition:

| Ingredient | Weight (mg) | % by weight of composition |
| --- | --- | --- |
| Purified water* EP/USP** | 465.0 | 93.0 |
| Spray dried fish gelatin | 20.0 | 4.0 |
| Mannitol EP/USP | 15.0 | 3.0 |
| TOTAL | 500.0 | 100.0 |

*signifies removal during the lyophilization process.
**EP European Pharmacopoeia
USP = United States Pharmacopoeia Comparative Example A Preparation of a Placebo Fast-Dispersing Dosage Form using Alkaline Bovine Hide Gelatin Alkaline bovine hide gelatin (4 g) was added to purified water (93 g) in a glass beaker and evenly heated to 60° C. while constantly stirring with a magnetic follower. Care was taken to ensure that all the gelatin had dissolved. The mix was then cooled to a temperature of 25° C. by means of a water bath before the addition of mannitol (3 g). When the mannitol had dissolved, stirring was continued for 1 hour at ambient conditions. This solution was then dosed into blister pockets, frozen, stored and freeze-dried as described in Example 1 above. The resultant units had the following composition:

| Ingredient | Weight (mg) | % by weight of composition |
| --- | --- | --- |
| Purified water* EP/USP | 465.0 | 93.0 |
| Alkaline bovine hide gelatin | 20.0 | 4.0 |
| Mannitol EP/USP | 15.0 | 3.0 |
| TOTAL | 500.0 | 100.0 |

*signifies removal during the lyophilization process.

The following additional comparative examples were prepared using the process described in Comparative Example A.

Comparative Example B

Preparation of a Placebo Fast-Dispersing Dosage Form Using Pig Skin Gelatin

A fast-dispersing dosage form using pig skin gelatin was prepared in a manner similar to that found in Comparative Example A, and the resultant units had the following compositions:

| Ingredient | Weight (mg) | % by weight of composition |
| --- | --- | --- |
| Purified water* EP/USP | 465.0 | 93.0 |
| Pig skin gelatin (Bloom 52 g) | 20.0 | 4.0 |
| Mannitol EP/USP | 15.0 | 3.0 |
| TOTAL | 500.0 | 100.0 |

*signifies removal during the lyophilization process.

Comparative Example C

Preparation of a Placebo Fast-Dispersing Dosage Form Using Limed Hide Gelatin

A fast-dispersing dosage form using limed hide gelatin was prepared in a manner similar to that found in Comparative Example A, and the resultant units bad the following composition:

| Ingredient | Weight (mg) | % by weight of composition |
| --- | --- | --- |
| Purified water* EP/USP | 465.0 | 93.0 |
| Limed hide gelatin (Bloom 70 g) | 20.0 | 4.0 |
| Mannitol EP/USP | 15.0 | 3.0 |
| TOTAL | 500.0 | 100.0 |

*signifies removal during the lyophilization process.

EXAMPLE 2

Comparative Tensile Strength and Dispersion Testing

The units produced in Example 1 and the Comparative Examples A through C were subjected to tensile strength and disintegration tests according to methods conforming to the USP monograph requirements. An additional dispersion test was also carried out to identify any subtle differences which may not be apparent from the disintegration test.

The dispersion test was performed by adding 500 ml volume of purified water into a glass beaker. The water was then heated to a temperature of 37° C. The units were carefully dropped onto the surface of the water and the time taken to fully disperse noted. The water was then changed for subsequent unit testing.

Results

The units produced in Example 1 exhibited a disintegration time of 0.85 seconds and gave a mean tensile strength value of 0.267 N mm$^{-2}$. In contrast, the units produced in Comparative Example A exhibited a disintegration time of 4.28 seconds and had a mean tensile strength value of 0.408 N mm$^{-2}$. The dispersion test confirmed these results. The units produced in Comparative Examples B and C exhibited a mean tensile strength of 0.407 N mm$^{-2}$ and 0.433 N mm$^{-2}$ respectively. In addition, it was noted that the units produced in Example 1 had no unpleasant smell or taste and a better mouth-feel than the units produced in the Comparative Examples. In particular, the units of Comparative Examples B and C were slow to disperse and had a gummy mouth-feel.

It is apparent from the above that fast-dispersing dosage forms produced using fish gelatin have a number of advantages over those produced using mammalian-derived gelatin. For instance, such dosage forms containing fish gelatin have a faster disintegration time, a better taste and a better mouth-feel than dosage forms containing mammalian derived gelatin. Moreover, there is no need for sweeteners and flavors to be added to mask the taste or smell of the gelatin since fish gelatin has an acceptable taste and smell. Thus, although some sweeteners and flavors may still be required to mask the taste of an unpalatable active ingredient, the overall quantity of sweeteners and flavors can be greatly reduced with attendant cost benefits. In addition, since fish gelatin is soluble in cold water, the heating step, which is required when mammalian derived gelatin is used, can be omitted thereby producing cost savings in heating costs and shorter mixing times. The overall process is therefore more controllable when fish gelatin is used in place of mammalian derived gelatin. The following examples further exemplify formulations which can be prepared using the process described in Example 1.

EXAMPLE 3

Fast-Dispersing Dosage Form using Fish Gelatin with Dextromethorphan as the Active Ingredient

| Ingredient | Weight (mg) | % by weight of composition |
| --- | --- | --- |
| Purified water* EP/USP | 909.0 | 90.9 |
| Fish gelatin | 40.0 | 4.0 |
| Mannitol EP/USP | 30.0 | 3.0 |
| Aspartame EP/USNF** | 4.0 | 0.4 |
| Mint Flavor | 2.0 | 0.2 |
| Dextromethorphan HBr | 15.0 | 1.5 |
| TOTAL | 1000.0 | 100.0 |

*signifies removal during the lyophilization process.
**USNF United States National Formulary A mean Tensile strength value of 0.206 N mm$^2$ was obtained for these dosage forms, with a disintegration time of 0.78 seconds.

EXAMPLE 4

Fast-Dispersing Dosage Form using Fish Gelatin

| Ingredient | Weight (mg) | % by weight of composition |
| --- | --- | --- |
| Purified water* EP/USP | 462.0 | 92.4 |
| Fish gelatin | 20.0 | 4.0 |
| Mannitol EP/USP | 15.0 | 3.0 |
| Aspartame EP/USNF | 2.0 | 0.4 |
| Mint Flavor | 1.0 | 0.2 |
| TOTAL | 500.0 | 100.0 |

*signifies removal during the lyophilization process.

These units had a mean Tensile strength value of 0.269 N mm$^2$, with a disintegration time of under 2 seconds.

EXAMPLE 5

Testing of "Gelling" Fish Gelatin

A formulation containing "gelling" fish gelatin was prepared and evaluated for disintegration time and mouth feel. Gelatin, mannitol and purified water were weighed into plastic vessels. The gelatin and mannitol were added to the vortex of continually stirred purified water, and the mixture was heated to a temperature of 60° C. in order to effect solution of the gelatin. Once dissolved, the solution was then cooled to a temperature of about 23.4° C. prior to dosing. Aliquots of 500 mg were dosed into pre-formed blister pockets and frozen, stored and freeze-dried.

A total batch of 100 grams was prepared containing the following formulation:

| Ingredient | Amount (% by weight) |
| --- | --- |
| Gelatin (117 g Bloom) | 4.0 |
| Mannitol (EP/USP) | 3.0 |
| Purified water (EP/USP) | 93.0 |
| TOTAL | 100 |

The dosage forms were analyzed for disintegration time and mouth feel. Disintegration time of the samples was measured according to USP methods. The samples had disintegration times of greater than 5 seconds. The mouth feel of the samples was found to be slow to disperse, "gummy" in nature, and overall unsatisfactory.

INDUSTRIAL APPLICABILITY

The pharmaceutical industry is constantly searching for improved dosage forms that are economical to produce and avoid problems associated with mammalian gelatin. The dosage forms according to the present invention addresses these needs and does so with superior results.

The invention has been described with reference to various specific and preferred embodiments and techniques. However, it should be understood that many variations and modifications can be made while remaining within the spirit and scope of the invention.

What is claimed is:

1. A process for preparing a pharmaceutical composition in a fast-dispersing dosage form having an active ingredient and fish gelatin carrier comprising a step of forming a network of the active ingredient and non-gelling fish gelatin carrier by subliming solvent from an admixture in the solid state in which the admixture comprises the active ingredient, the carrier and a solvent for the carrier.

2. A method of using fish gelatin as a carrier in pharmaceutical composition comprising:
   a) adding fish gelatin in a solvent to an active ingredient to form an admixture;
   b) freezing said admixture; and
   c) subliming the solvent from the frozen admixture, wherein the composition is in fast-dispersing dosage form which releases the active ingredient rapidly on contact with fluid.

3. A method according to claim 2, wherein the composition disintegrates within 1 to 60 seconds of being placed in contact with fluid.

4. A method according to claim 2, wherein the composition is designed for oral administration and releases the active ingredient rapidly in the oral cavity.

5. A method according to claim 2 wherein the fish gelatin is non-gelling fish gelatin.

6. A method according to claim 5 wherein the fish gelatin is non-hydrolyzed.

7. A method according to claim 6 wherein the fish gelatin is spray-dried.

* * * * *